US012576285B2

(12) United States Patent
Wu et al.

(10) Patent No.: US 12,576,285 B2
(45) Date of Patent: Mar. 17, 2026

(54) SYSTEM OF FILMLESS REAL-TIME QUALITY ASSURANCE FOR BEAM ALIGNMENT FOR RADIOSURGERY SYSTEMS

(71) Applicants: Xiaodong Wu, North Miami Beach, FL (US); Benjamin Pomper, Hollywood, FL (US); Mark Pomper, Miami Beach, FL (US)

(72) Inventors: Xiaodong Wu, North Miami Beach, FL (US); Benjamin Pomper, Hollywood, FL (US); Mark Pomper, Miami Beach, FL (US)

( * ) Notice: Subject to any disclaimer, the term of this patent is extended or adjusted under 35 U.S.C. 154(b) by 188 days.

(21) Appl. No.: 18/673,272

(22) Filed: May 23, 2024

(65) Prior Publication Data

US 2024/0390702 A1     Nov. 28, 2024

Related U.S. Application Data

(60) Provisional application No. 63/503,770, filed on May 23, 2023.

(51) Int. Cl.
*A61N 5/10*          (2006.01)

(52) U.S. Cl.
CPC ......... *A61N 5/1075* (2013.01); *A61N 5/1083* (2013.01); *A61N 2005/1076* (2013.01)

(58) Field of Classification Search
CPC ............... A61N 5/1075; A61N 5/1083; A61N 2005/1076
See application file for complete search history.

(56) References Cited

U.S. PATENT DOCUMENTS

2018/0339174 A1 * 11/2018 Kilby ................... A61N 5/1065
2019/0000564 A1 * 1/2019 Navab ................. H04N 13/254

* cited by examiner

*Primary Examiner* — Uzma Alam
*Assistant Examiner* — Mamadou Faye
(74) *Attorney, Agent, or Firm* — David W Barman

(57) ABSTRACT

The present invention is a system for providing accurate image-guided localization of a radiation target using digital image acquisition with real time data analysis utilizing a radiation device, directing a beam of radiation through a sample reflecting onto a film screen and reflecting an image from the film screen onto a mirror that will project the image from the mirror to a bean splitter where it is captured by a camera operatively associated with a computer device.

5 Claims, 7 Drawing Sheets

SYSTEM OF FILMLESS REAL-TIME QUALITY ASSURANCE FOR BEAM ALIGNMENT FOR RADIOSURGERY SYSTEMS

CROSS-REFERENCE TO RELATED APPLICATIONS

This application is a non-provisional of and claims benefit to U.S. provisional patent application Ser. No. 63/503,770 filed May 23, 2023 the disclosure of which is incorporated hearing by reference in its entirety.

BACKGROUND OF THE INVENTION

Advances in radiation physics and computer technology made it possible to aim radiation more precisely to treat cancer or other clinical conditions. Stereotactic radiosurgery (SRS) or Stereotactic Body Radiotherapy (SBRT) utilizes targeted high dose radiation to ablate a lesion. This is often accomplished through image-guided localization of the target using many beams of radiation penetrating from different angles in efforts to diminish dose to the adjacent normal structures. SRS/SBRT treatment relies fundamentally on accurate deliverance of radiation dose. Minor errors in the beams' placement of the radiation dose may result in erroneous measures of the cumulative dose that the tumor receives as well as the dosage that the nearby organs receive.

In order to maintain accurate beam placement and alignment quality assurance tests are routinely performed. An automated quality assurance test (AQA) is an isocentric targeting accuracy testing device developed by Accuray, Inc, a California company for the Cyberknife® SRS/SBRT system. The AQA presently being used has certain disadvantages, namely that it requires disposable radiographic film which is costly. Furthermore, it does not provide the operator with real time analysis, which makes the quality assurance test time consuming. Due to the inefficiency of this process, there is a need to develop a new or improved AQA device that is more efficient and cost effective.

The present invention addresses this need.

SUMMARY OF THE INVENTION

In one embodiment of the present invention, an AQA phantom is positioned at the top of the device. A first x-ray beam will pass through the phantom and produce a lateral QA image on the fluorescent screen. A mirror angled at 45-degree angle relative to a fluorescent screen placed behind the fluorescent screen and will reflect this image downward towards a beam splitter. The beam splitter will reflect the image with approximately 50% of its intensity towards the camera.

Then, a second x-ray beam will pass through the phantom in the AP (Anterior to Posterior) direction and produced the QA image on second fluorescent screen. The second mirror is positioned at a 45-degree angle behind the second fluorescent screen. This mirror will reflect the image towards the beam splitter which in turn will allow the image to be transmitted with approximately 50% of its intensity towards the camera.

By using fluorescent screens, the present invention eliminates the need of any film and the associated costs. Additionally, the camera will be remotely controlled outside the radiation room and connected to a computer that is also outside of the radiation room. Via this connection images can be analyzed in real time, allowing the operator to verify and adjust any alignment of the radiation beam if necessary.

The current AQA method uses gafchromic film which is costly. The present invention uses fluorescent screens to capture images, which have a long lifetime of reusability.

The current AQA method requires retrieval of the film after exposure, scanning of the films, loading into an independent software to the analyzed for concentricity. The present invention captures and analyzes the images within the software without ever having to even enter the treatment room to retrieve anything.

The current AQA method can be cumbersome when needing to make alignment adjustments. The present invention uses the same setup without needing to move and to reposition the device while providing real-time update during re-alignment.

The present invention captures and analyzes images in real-time so it's more efficient.

In one embodiment the system is used in the following steps:

1) Position the test cube onto the invention in the proper orientation
2) Connect the invention to the computer outside the radiation room
3) Irradiate the test cube in the AP direction
4) The radiation illuminates the sphere held within the cube onto the bottom fluorescent screen
5) The bottom mirror reflects the image towards the beam splitter
6) The beam splitter allows approximately 50% of transmission of the image to pass through to the camera lens
7) The Camera sees the image
8) Manual operator of the computer captures as many images as desired adjusting the gain and exposure for ideal image contrast in the Acquisition application
9) After irradiating in the AP position the robot automatically moves into the lateral position
10) Irradiate the test cube in the lateral direction
11) The radiation illuminates the sphere held within the cube onto the top fluorescent screen
12) The top mirror reflects the image towards the beam splitter
13) The beam splitter reflects approximately 50% of the image to the camera lens
14) The camera sees the image
15) Manual operator of the computer captures as many images as desired adjusting the gain and exposure for ideal image contrast in the Acquisition application Once the images are captured . . .

16) Load calibration image into the Calibration application to determine the mm/pixel
17) Load the AP and lateral images taken into the Calculation application
18) Select the area to analyze
19) Click calculate.

In one embodiment, the present invention is A system for providing accurate image-guided localization of a radiation target using digital image acquisition with real time data analysis, said system comprising:

a housing;

a camera having a lens positioned in a lens cavity of said housing, said camera having an input-output data port configured thereon an upper mirror;

a lower mirror, wherein each of said upper mirror and lower mirror are parallel one to another;

a beam splitter positioned parallel and between each of said upper mirror and lower mirror;

a testing cube support configured to hold a testing cube; wherein said system is configured for use with an existing radiation emitting device wherein said device includes a lens for directing a beam from said device into said testing cube.

In one embodiment, the housing includes an upper mirror slot and a lower mirror slot configured at a 45 degree angle relative to a vertical wall of said housing wherein each of said upper mirror slot and lower mirror slot are parallel one to another.

In one embodiment, the camera has a resolution between 10 and 100 megapixels and preferably a resolution between 12 and 20 megapixels.

In one embodiment, the beam splitter constructed of borosilicate optical glass with high transmission and is free of bubbles and inclusions.

DETAILED DESCRIPTION OF THE INVENTION

Figure 1:
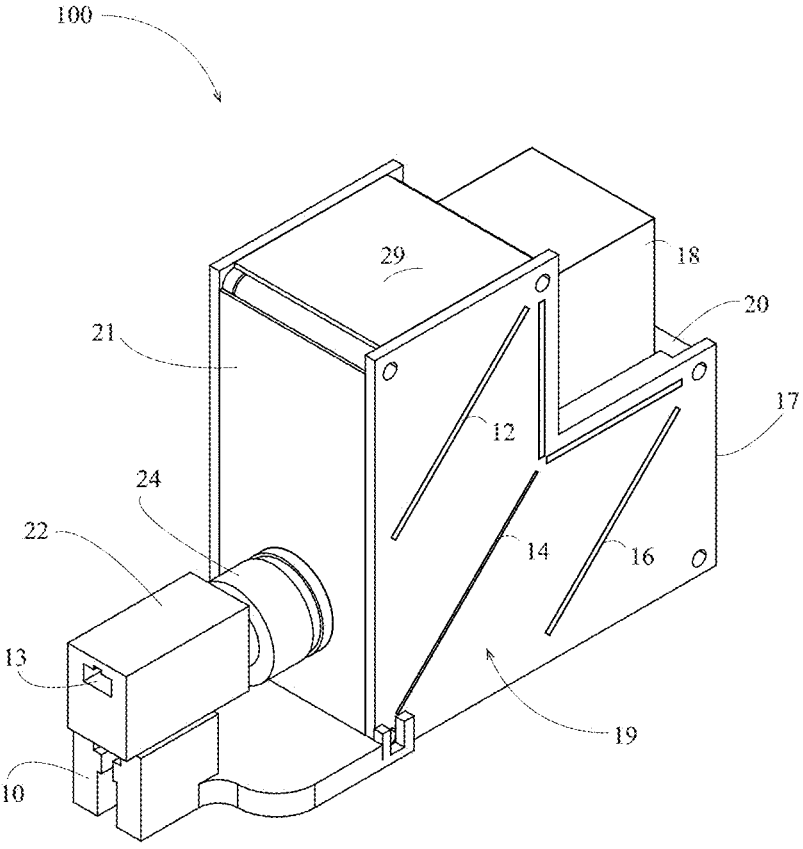
FIG. 1 is a perspective view according to one embodiment of the present invention.
Figure 2:
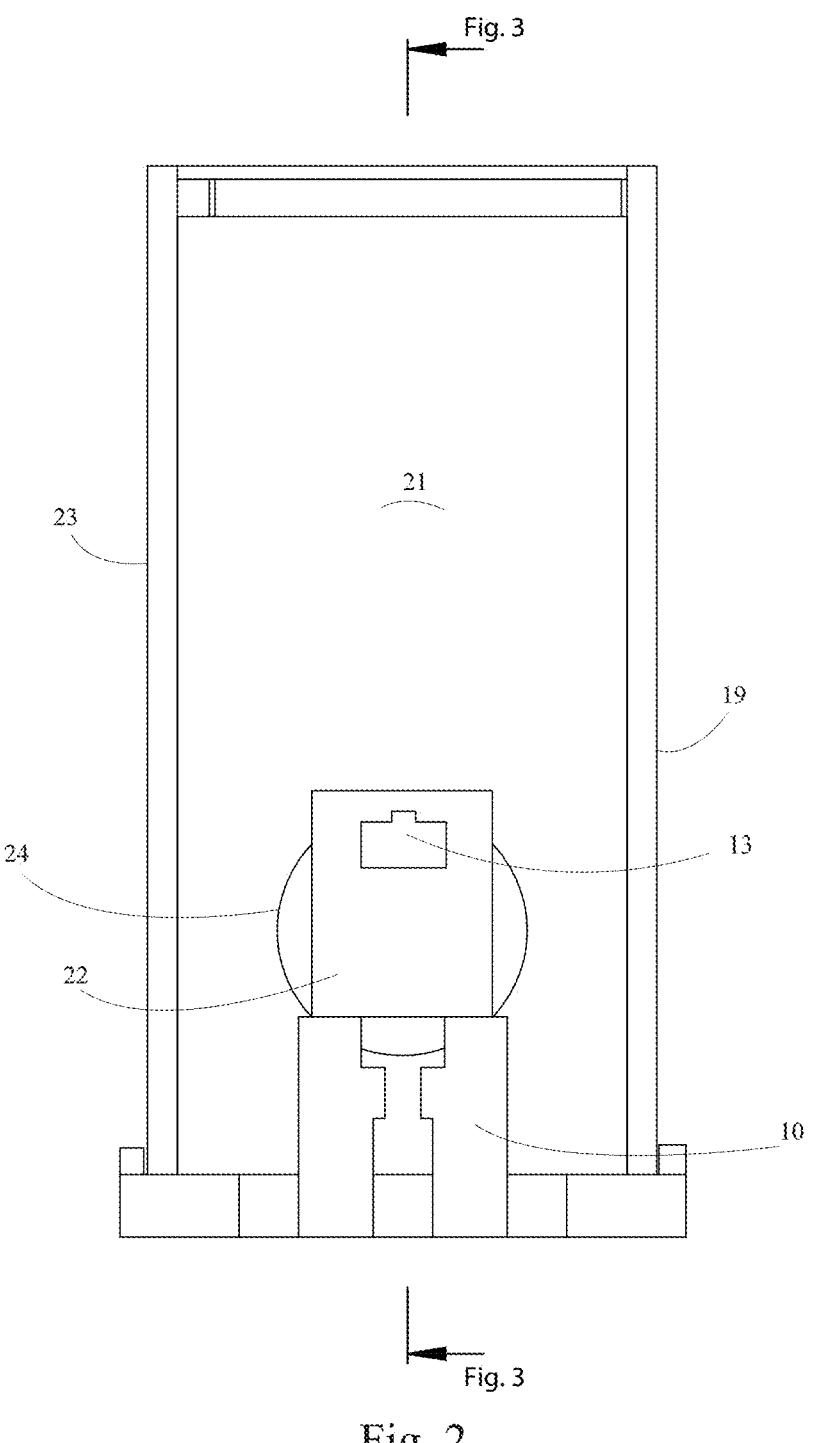
FIG. 2 is a back view according to one embodiment of the present invention.

As understood by the Figures and description herein, the present invention is a system including fluorescent screens, a mirror assembly, and a camera. The system is constructed and arranged and will capture images for subsequent real time data analysis.

The tables set forth below provide information relating to the configuration of the system. They are preferred configurations but in no way are limiting or exhaustive of desired configurations. Systems are thus configurable as long as they functionally carry out the desired results of the invention.

TABLE 1

| External Casing of the invention. External Casing | |
| --- | --- |
| Material | PLA |
| Manufacturing | 3D Printed |
| Size | 12.8 × 8.3 × 6.7 inches (326 × 211 × 169 mm) |

TABLE 2

| Screen Configuration X-Ray Intensifying Screen | |
| --- | --- |
| Brand | Kiran Rare Earth Green Screens (Speed: 400) |
| Dimensions (Length × Width) | 2 × 2 inches (50.8 × 50.8 mm) |
| Composition | Terbium-activated gadolinium oxy-sulfide phosphor |

TABLE 3

| Reflective Mirror | |
| --- | --- |
| Construction | Plate |
| Dimensions (Length × Width) | 3 × 3 inches (76.2 mm × 76.2 mm) |
| Thickness | 0.236 inches (6.00 mm) |
| Substrate | Float Glass |
| Coating Type | Metal |
| Coating | Protected Aluminum (400-2000 nm) |
| Coating Specification: | Ravg > 85% @ 400-700 nm |
| | Ravg > 90% @ 400-2000 nm |

TABLE 4

| Beam Splitter Configuration BeamSplitter | |
| --- | --- |
| Construction | Plate |
| Dimensions (Length × Width) | 2.95 × 2.95 inches (75.0 mm × 75.0 mm) |
| Thickness | 0.118 inches (3.00 mm) |
| Reflection/Transmission Ratio | 50/50 |
| Wavelength Range | 400 nm-700 nm |
| Substrate | N-BK7 |

TABLE 5

| Camera Configuration Image Detector Camera | |
| --- | --- |
| Brand | The Imaging Source DMK 33GX236 |
| Color | Black |
| Focus Type | Automatic |
| ISO Range | 100-12800 |
| Dimensions | 8.8 × 5.4 × 6.6 in |
| | (223.5 × 137.16 × 167.64 mm) |
| Max Resolution | 18 megapixels |
| Optical Zoom | 3.1× |
| EF-S | 18-55 mm |
| Focal Length | 3.5-3.6 |
| Frames Per Second Shooting | 3 |

System 100 of the present invention includes a back panel 21 constructed in a range to accommodate a camera lens 24 of camera 22, whereby said camera 22 is upon camera support base 10. Camera is further configured with communications port 13 as is commonly known. Port 13 is an input-output data transmission port constructed and arranged to receive a data transmission cable. System 100 further includes top mirror 12, beam splitter 14, and bottom mirror 16. Testing cube 18 is positioned on system 100 as shown in the figures. The beam splitter 28 is constructed of borosilicate optical glass with high transmission and is free of bubbles and inclusions. In one preferred embodiment, SCHOTT N-BK7® is utilized as the borosilicate optical glass.

The system includes housing 17 that is formed by right side panel 19 front panel 21 left side panel 23 back panel 25 top panel 29 and underside panel 33. Additionally, support 20 and sample wall 37 collectively as part of support housing 17 define internal housing cavity 35. Each of beam splitter 28 top mirror 30 and bottom mirror 32 are positioned within internal housing cavity 35. As generally understood by the drawings top mirror 30 is inserted through either right side top mirror insertion cavity 12 or left side top mirror insertion cavity 54. Regardless of which cavity top mirror 30 is inserted, top mirror 30 will rest in position being held into place, while resting on the lower portion of each of right side top mirror insertion cavity 12 and left side top mirror insertion cavity 54. Similarly, bottom mirror 32 is inserted through either right side bottom mirror insertion cavity 16 or left side bottom mirror insertion cavity 72. In a similar manner, bottom mirror 32 rests in position along the lower edge of each of the complementary right side bottom insertion cavity 16 and left side bottom mirror insertion cavity 72. Also, in a similar fashion, beam splitter 28 is inserted through either right side beam splitter insertion cavity 14 or left side beam splitter insertion cavity 57. Beam splitter 28 will rest in position along the lower edge of each of the complementary right side beam splitter, and section cavity 14 and left side beam splitter insertion cavity 57. Top mirror 30 includes first top mirror alignment mark 58 second top mirror alignment mark 60 and third top mirror alignment mark 62. When mirror 30 is inserted into cavity 35, each of the alignment marks are configured for aligning and directing a beam from beam collimator 42. Bottom mirror 32 includes first bottom mirror alignment mark 66 second bottom mirror alignment mark 68 and third bottom mirror alignment mark 70. When bottom 32 is inserted into cavity 35 each of the alignment marks are configured for aligning and directing a beam from beam collimator 42.

The invention further includes utilization of a radiation device 46 that is adjustable along radiation device hinges 44 where by radiation device 46 has a beam collimator 42 that is aimed at testing cube 18 having sample alignments sphere 40 place their in.

Figure 3A:
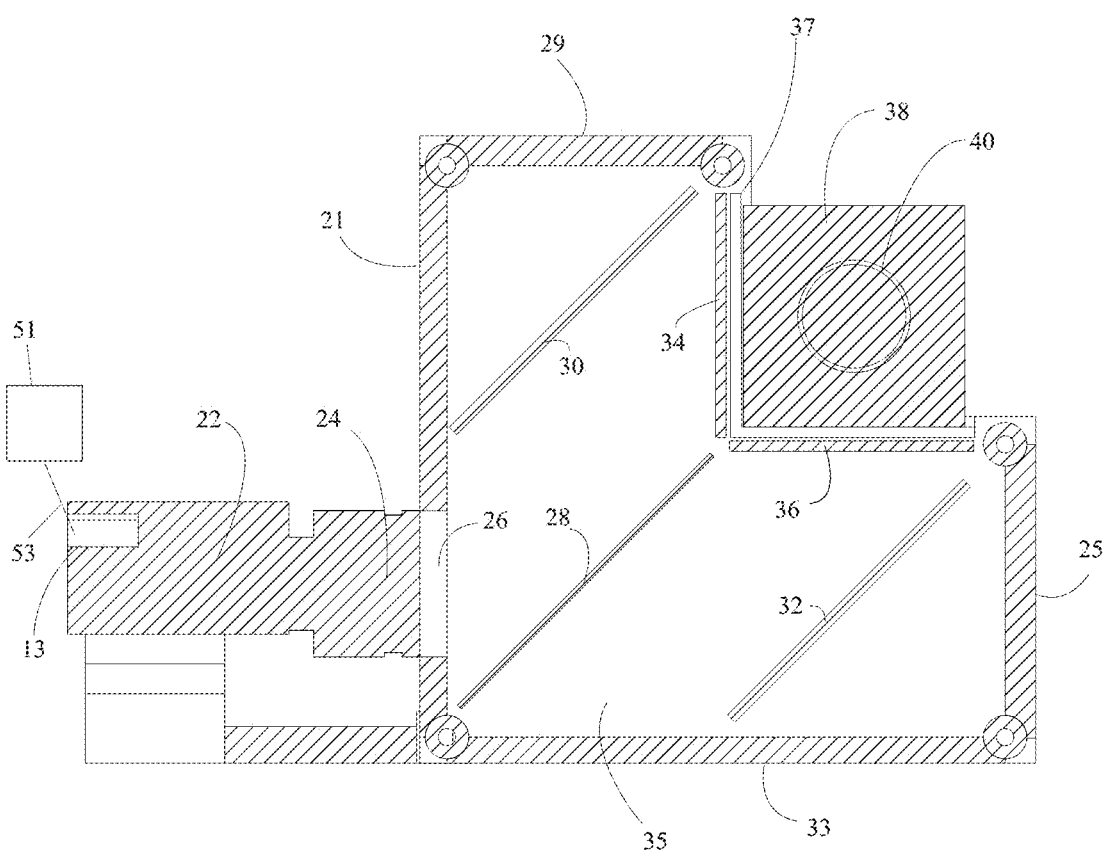
FIG. 3A is a side partial cross section view according to one embodiment of the present invention.
Figure 3B:
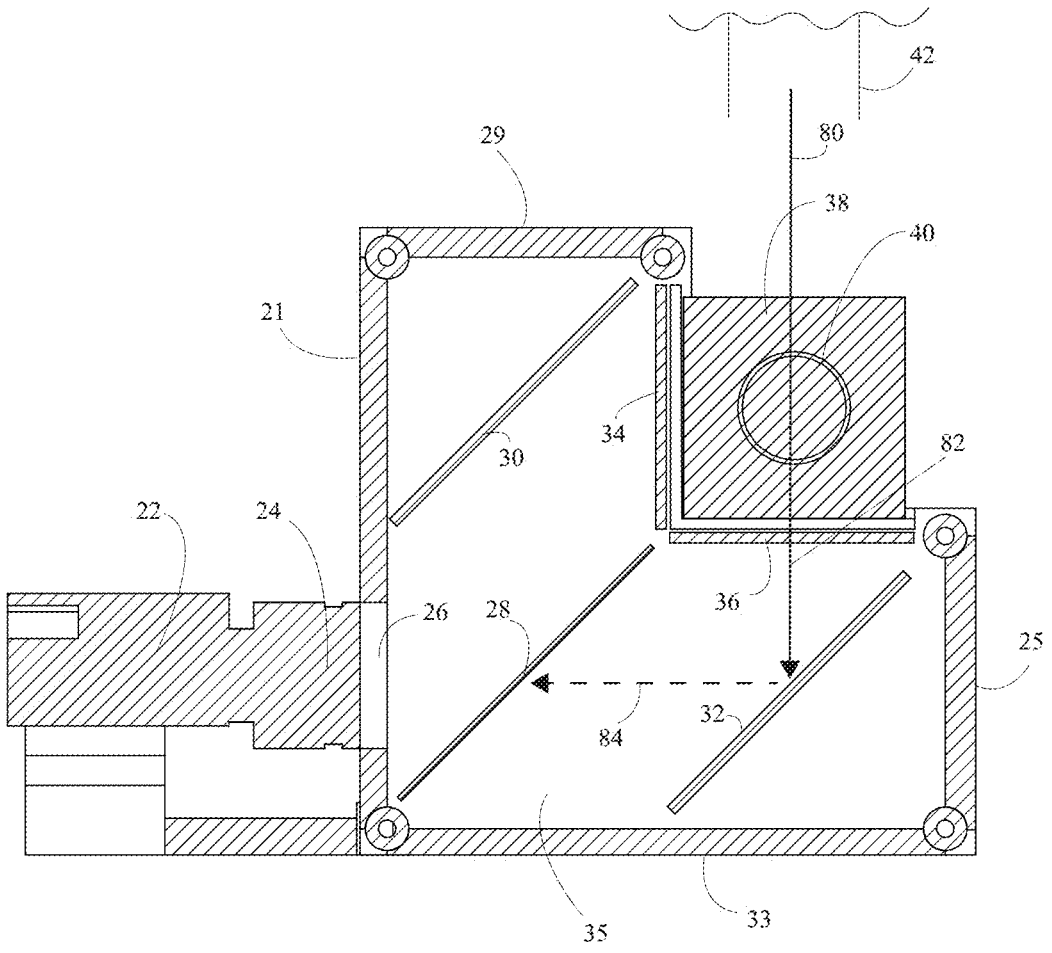
FIG. 3B is a side partial cross section view demonstrating beam direction from above according to one embodiment of the present invention.

In an embodiment demonstrated and FIG. 3B, radiation beam 80 is directed from Beam collimator 42 and passes through alignment sphere 40. Placed horizontally below testing cube 38 is bottom film screen 36. When radiation from beam 80 contacts bottom film screen 36 at bottom film illumination interface 82. Bottom film screen 36 illuminates and projects an image downward onto the lower mirror 32 image is transmitted to beam splitter 28 along lower mirror path 84 and camera 22 captures an image. In many embodiments, the shutter release is controlled from the computer application. The invention connects to the computer through a typical ethernet cable or similar connection device.

Figure 3C:
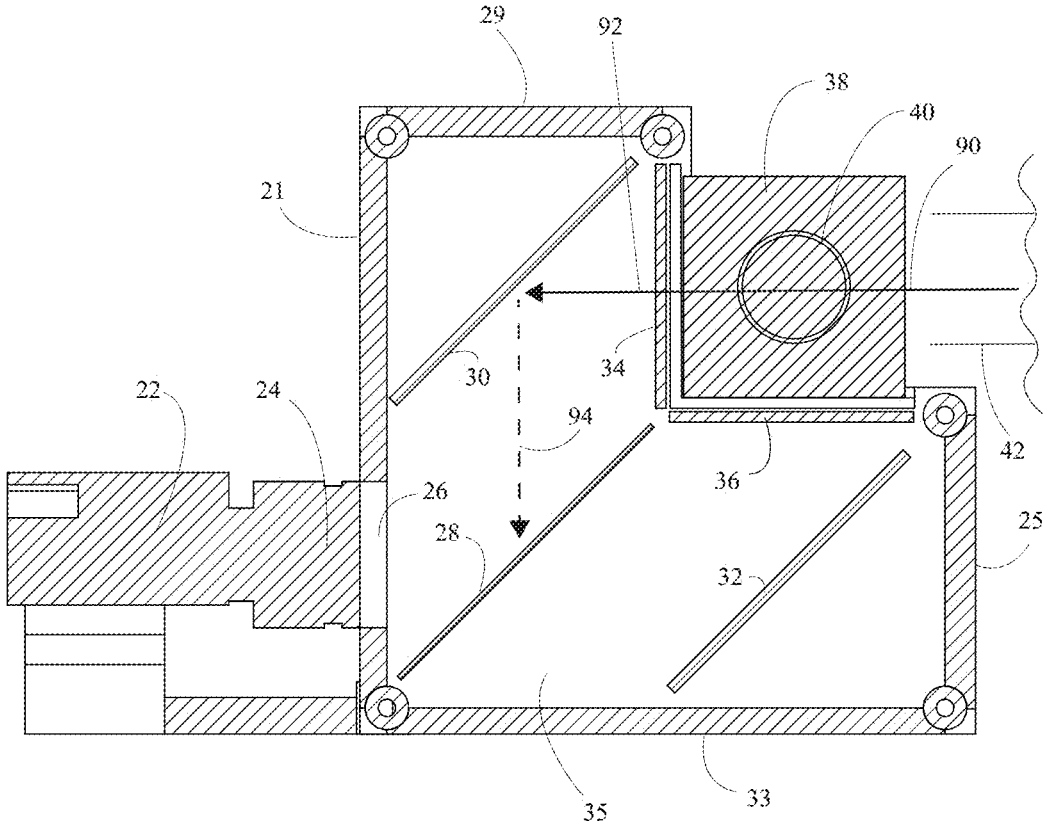
FIG. 3C is a side partial cross section view demonstrating beam direction from the side according to one embodiment of the present invention.
Figure 4:
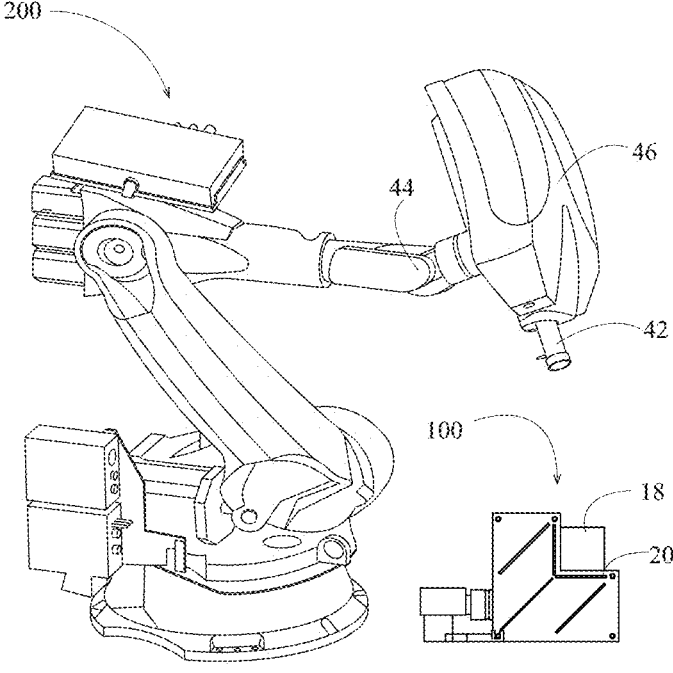
FIG. 4 is a side perspective view according to one embodiment of the present invention.
Figure 5:
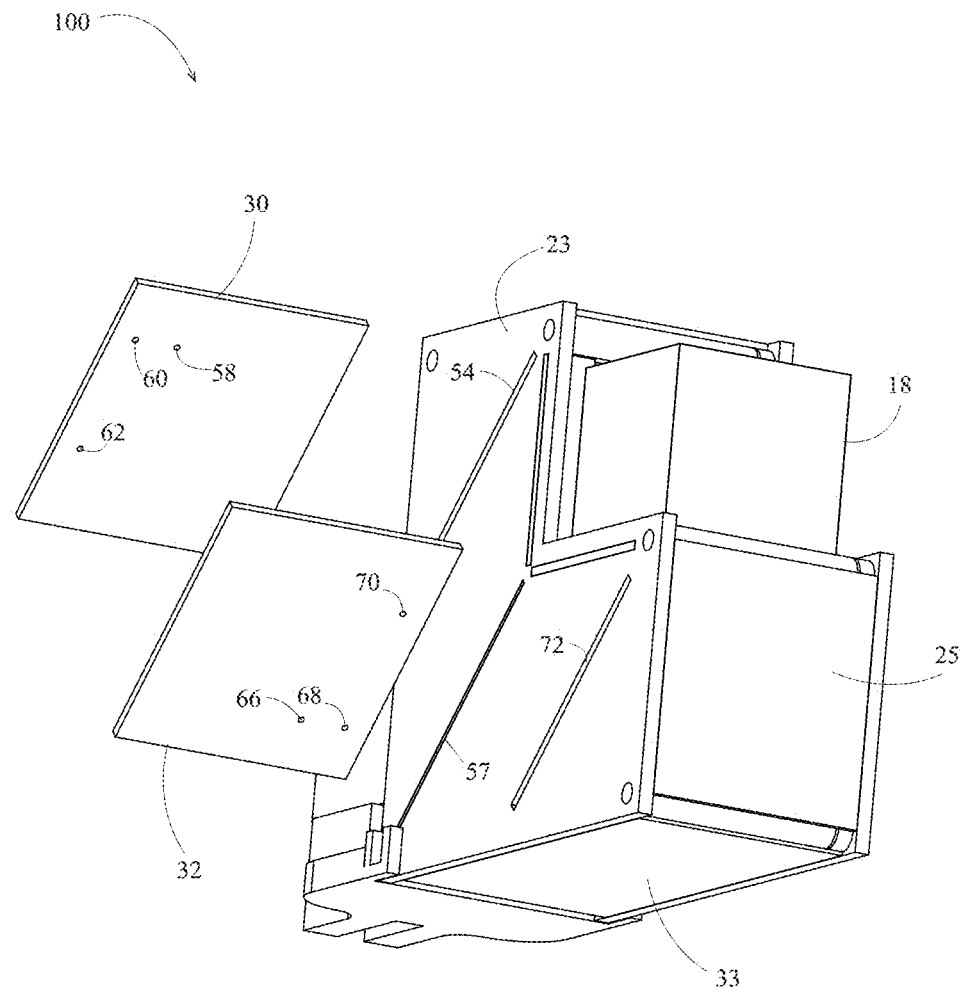
FIG. 5 is a side perspective partial exploded view according to one embodiment of the present invention.

In an embodiment demonstrated in FIG. 3C, radiation beam 90 exits from beam collimator 42 positioned horizontally behind testing cube 38. Radiation beam 90 passes through alignment sphere 40 and illuminates top film screen 34 at top film illumination interface 92. An image from top film screen 34 is projected onto top mirror 30 and reflected along top mirror projection path 94 onto beam splitter 28. This image is captured by 22.

The specific contemplated characteristics for each of top film screen 34 and bottom film screen 36 are set forth table 2 herein.

The specific characteristics for each of top mirror 30 and bottom mirror 32 are set forth in table 3 herein.

As understood and demonstrated by FIG. 3B, in this embodiment lens 42 of radiation device 46 is aimed from above at testing cube 18.

In the environment demonstrated by FIG. 3C, beam collimator 42 of radiation device 46 is aimed horizontally at testing cube 18.

In either of the horizontal or vertical/above application of a beam from beam collimator 42, the appropriately positioned film screen being either top film screen 34 or bottom film screen 36 is illuminated.

As generally understood a sample to be analyzed is positioned within testing cube 38. Beam 42 of radiation device 46 is aligned with testing cube 38 using alignment sphere 40 that is visible on the outside of testing cube 38. A beam of radiation is passed through testing cube 38 and, dependent on the position of beam collimator 42 will illuminate the appropriate film screen being either film screen 34 or bottom film screen 36. The illuminated image is projected onto the corresponding mirror to each film screen. As demonstrated in the figures, top mirror 30 is constructed, arranged, and positioned to reflect an image from top film screen 34. Bottom mirror 32 is constructed, arranged, and positioned to reflect an image from bottom film screen 36. Beam splitter 28 is positioned for receipt and reflection of an image from either top mirror 30 or bottom mirror 32. When image is projected onto beam splitter 28 camera lens 24 associated with camera 22 which is appropriately positioned by camera lens 26 to capture, an image on beam splitter 28. Camera 22 is operatively associated through an integrated input output port 13 to a computing device 51. The computing device 51 is configured to control camera 22 and capture an image. In one embodiment, input output port 13 has wire 53 for direct connection between camera 22 and computing device 51. Although the figure demonstrates a wired connection, any suitable connection for connecting computing device 51 to camera 22 is contemplated. This includes wireless, Bluetooth, and the like.

The system of the present invention is constructed and arranged to measure and calibrate the accuracy if the beam emitted from the beam generation device of the system.

Although the invention has been described with reference to specific embodiments and drawings, it is to be understood that the invention is not limited to those precise embodiments, and that various changes and modifications may be effected by one skilled in the art without departing from the scope or spirit of the present invention.

The invention claimed is:

1. A system for providing accurate image-guided localization of a radiation target using digital image acquisition with real time data analysis, said system comprising:
   a housing;
   a camera having a lens positioned in a lens cavity of said housing, said camera having an input-output data port configured thereon an upper mirror;
   a lower mirror, wherein each of said upper mirror and lower mirror are parallel one to another;
   a beam splitter positioned parallel and between each of said upper mirror and lower mirror;
   a testing cube support configured to hold a testing cube; wherein said system is configured for use with an existing radiation emitting device wherein said device includes a lens for directing a beam from said device into said testing cube.

2. The system of claim 1 wherein said housing includes an upper mirror slot and a lower mirror slot configured at a 45 degree angle relative to a vertical wall of said housing wherein each of said upper mirror slot and lower mirror slot are parallel one to another.

3. The system of claim 1 wherein said camera has a resolution between 10 and 100 megapixels.

4. The system of claim 1 wherein said camera has a resolution between 12 and 20 megapixels.

5. The system of claim 1 wherein said beam splitter constructed of borosilicate optical glass with high transmission and is free of bubbles and inclusions.

* * * * *